United States Patent [19]

Ancillotti et al.

[11] 4,071,567
[45] Jan. 31, 1978

[54] PROCESS FOR THE PRODUCTION OF METHYL TERT-BUTYL ETHER

[75] Inventors: Francesco Ancillotti, San Donato Milanese; Gianni Oriani; Ermanno Pescarollo, both of Milan, all of Italy

[73] Assignee: Snamprogetti S.p.A., Milan, Italy

[21] Appl. No.: 713,981

[22] Filed: Aug. 12, 1976

Related U.S. Application Data

[63] Continuation of Ser. No. 579,661, May 21, 1975, abandoned.

[30] Foreign Application Priority Data

May 21, 1974 Italy .................................. 23013/74

[51] Int. Cl.$^2$ ....................... C07C 41/06; C06C 41/10
[52] U.S. Cl. ............................. 260/614 A; 260/680 R
[58] Field of Search ................ 260/614 A, 614 R, 616

[56] References Cited

U.S. PATENT DOCUMENTS 1,968,601  7/1934   Edlund et al. ............... 260/614 A X
2,480,940  9/1949   Leum et al. ..................... 260/614 A
3,119,766  1/1964   Voltz et al. ................. 260/614 A X

FOREIGN PATENT DOCUMENTS 957,000    4/1964   United Kingdom ............ 260/614 A
1,176,620  1/1970   United Kingdom ............ 260/614 A Primary Examiner—Howard T. Mars
Attorney, Agent, or Firm—Morgan, Finnegan, Pine, Foley & Lee

[57] ABSTRACT

Methyl tert-butyl ether of high purity is prepared by reacting methanol with isobutylene in the presence of an acid ion exchange resin in two stages by feeding methanol and isobutylene mixed with other hydrocarbons to the respective members of a pair of interconnected reactors so that the quantity of alcohol present in one of the reactors is in excess of the stoichiometric equivalent of the quantity of isobutylene therein, while the quantity of isobutylene present in the other reactor is in excess of the stoichiometric equivalent of the quantity of methanol therein, and the methyl tert-butyl ether so formed is recovered through distillation.

6 Claims, 2 Drawing Figures

PROCESS FOR THE PRODUCTION OF METHYL TERT-BUTYL ETHER

This is a continuation of application Ser. No. 579,661 filed May 21, 1975, now abandoned.

The present invention relates to a process for the production of tert-alkyl ethers.

It is known that a tert-alkyl ether can be prepared by reacting a primary alcohol with an olefin having a double bond on a tertiary carbon atom, as methanol reacts with isobutylene or isoamylenes (2 methyl butene 1 or 2) to form respectively methyl tert butyl ether (MTBE) and methyl tert-amyl ether: (MTAE).

The reaction is so selective for tertiary olefins that it constitutes a valid process for their removal from olefinic streams wherein they are contained together with linear unreactive olefins.

The reaction has an equilibrium which is more favourable to the synthesis of the ether the lower the reaction temperature in accordance with its negative enthalpy.

It is known that the reaction is catalized by Lewis acids (aluminium trichloride, boron trifluoride), mineral acids (sulphuric acid) and organic acids (alkyl and aryl sulphonic acids, ion exchange resins).

Particularly suitable to the task are the ion exchange resins in their acid form and it is known that the best results are obtained in fact with macroreticular resins of the "Amberlyst 15" type. By means of such catalysts it is possible to reach thermodynamic equilibrium within industrially acceptable contact times, at temperatures in the range of 50°–60° C. At lower temperatures, thermodynamically more favourable, the kinetics are not sufficiently favorable to permit reaching equilibrium in practice. This fact limits conversions; in fact in the case of isobutylene and methanol, used at equimolecular ratios the conversions reached were not higher than 92%.

Obviously the conversion of a reagent can be increased by increasing in the feed the content of the other reagent but this involves a lowering of the conversion of the reagent in excess. This can cause some drawbacks such as those which occur in the synthesis of MTBE starting from methanol and isobutylene contained in an olefinic stream.

The use of an excess of isobutylene involves, as a consequence, the fact that the olefinic stream, after separation of MTBE, still contains 5–10% isobutylene and this constitutes a drawback when said stream is utilized for the production of maleic anhydride or butadiene; on the other hand an excess of methanol renders very heavy the purification of MBTE because of the formation of azeotropes.

The subject of the present invention is a process which makes it possible to reach a high conversion for both reagents and this has not been accomplished heretofore.

An object of the present invention is the obtaining of a high conversion for both reagents even though they are maintained in totally stoichiometric ratios.

All this can be accomplished by carrying out the reaction in two distinct reactors and feeding the reagents in such a way that in one of the reactors there is a substantial excess of one of them while in the second reactor there is an excess of the other reagent.

A further object of the present invention is to furnish a process for the production of tert-butyl ethers starting from isobutylene and alcohols with a great excess of olefin without collateral reactions of oligomerization of isobutylene.

That object can be reached by working at an olefin space velocity in the range of from 20 to 50 LHSV.

Figure 1:
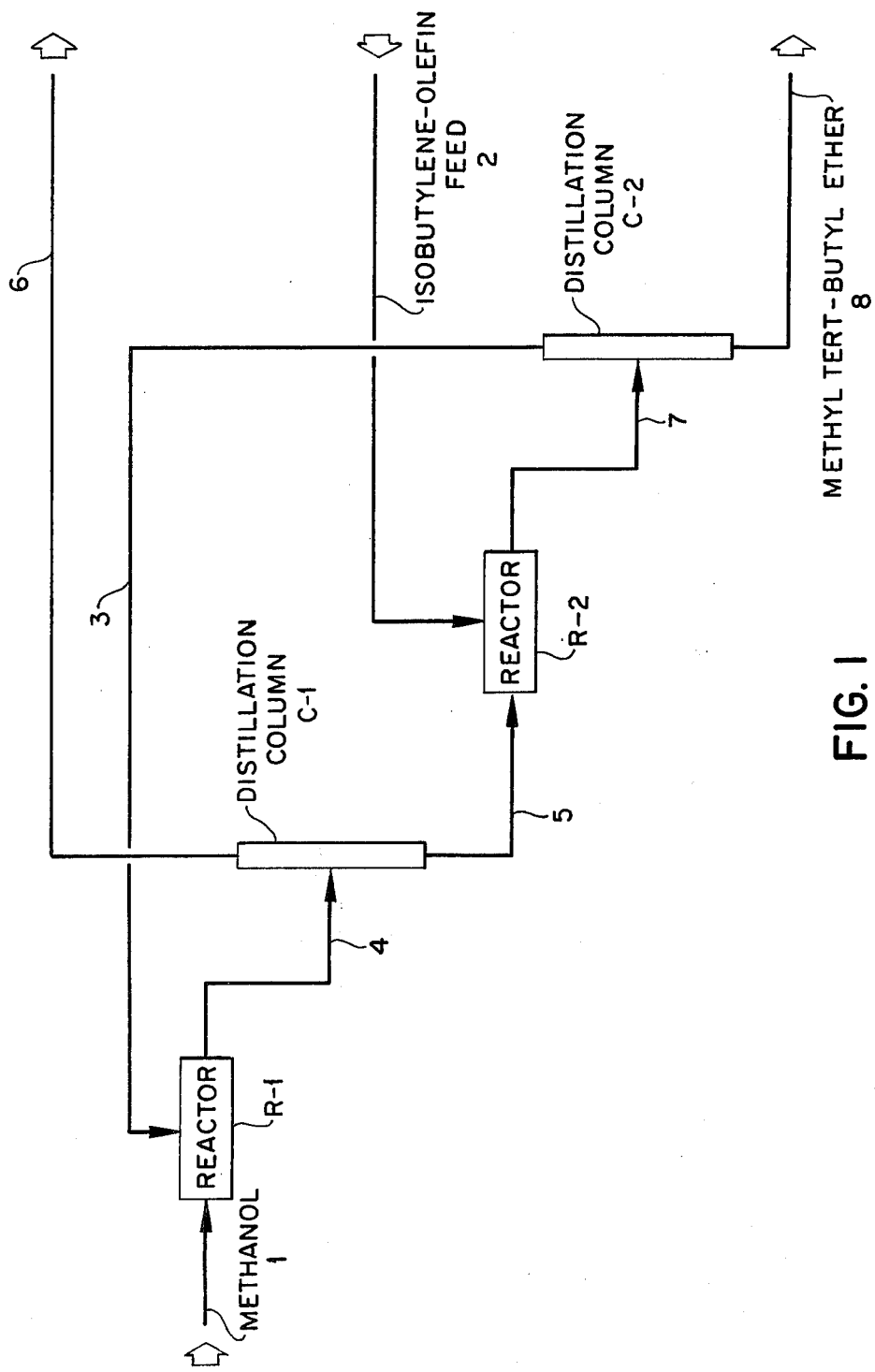
FIG. 1 is a schematic illustration of a method of carrying out our invention.

The synthesis of methyl ter-butyl ether starting from methanol and isobutylene, for example, can be carried out in accordance with the scheme in FIG. 1.

Methanol (1) is fed to a reactor R-1 together with the effluent stream (3) from the top of column C-2, constituted by an olefinic stream from which some isobutylene had been removed as described below.

That reaction mixture in R-1 contains an excess of methanol so that isobutylene conversion is very high.

The effluent stream (4) from R-1 enters distillation column C-1 from the top of which an olefinic fraction (6) is obtained wherein the isobutylene content is lower than 2%. From the bottom of Column C-1 a mixture (5) of methanol and MTBE is obtained.

The bottom stream (5) from C-1 mixed with the olefinic feed (2) is introduced into reactor R-2. The reaction mixture in R-2 contains an excess of isobutylene so that methanol conversion is high.

The product (7) leaving reactor R-2 enters distillation column C-2 from the bottom of which MTBE (8) of a high degree of purity is discharged and from the top of which an olefinic stream (3) deprived of isobutylene is discharged which is recycled to R-1.

In reactor R-2 wherein we work with a strong excess of isobutylene it is possible to have secondary oligomerization reactions of isobutylene and this is what actually occurs by working at 60°–70° C and space velocities LHSV of 5–10.

The phenomenon can be minimized by distributing the olefine feed both to reactor R-1 and to reactor R-2 (see Example 2).

It has been found, however, that it is possible to obtain high selectivities also in the presence of an excess of isobutylene, by working at 60° C and LHSV of 40, without lowering conversion to MTBE.

Figure 2:
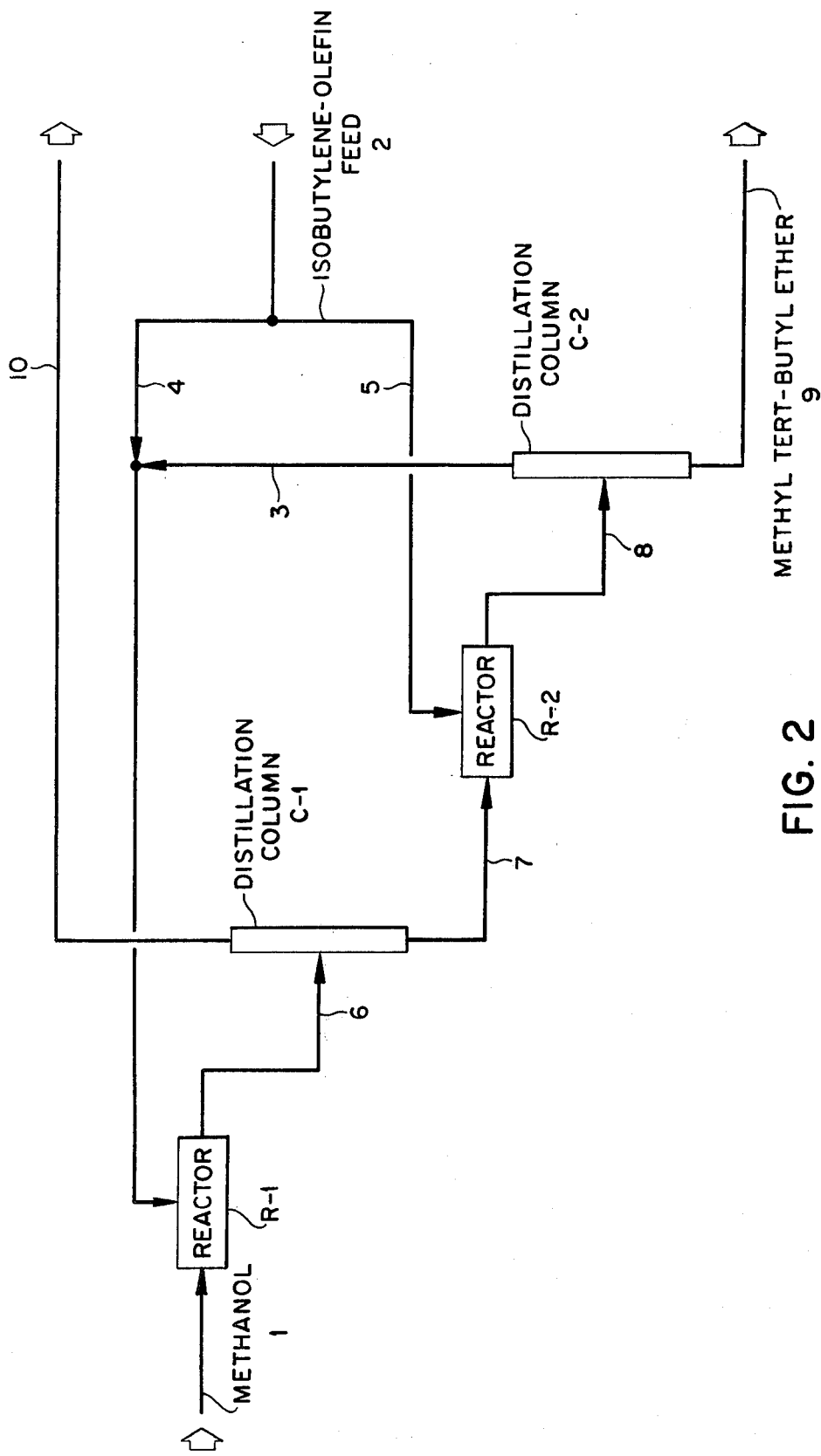
FIG. 2 is a schematic illustration of a modification in the process illustrated in FIG. 1.

The scheme according to FIG. 2 represents a variant of the process represented in FIG. 1 in which the olefine is fed not only to R-2 but is distributed between R-2 and R-1.

EXAMPLE 1

The operation was carried out in accordance with FIG. 1.

21.11 parts by weight of methanol (1) were joined to the stream (3) leaving the top of column C-2, constituted by 23.38 parts of isobutylene, 43.43 parts of linear olefines and 0.35 parts of methanol. The mixture, in which the isobutylene-methanol molar ratio — was 0.62, was fed to reactor R-1 wherein it reacted in the presence of Amberlyst 15 at a temperature of 60° C with LHSV of 5 volumes per hour per volume of catalyst and at a pressure sufficient to maintain the system in the liquid phase.

The effluent stream (4) from reactor R-1, which was constituted by 8.46 parts of methanol, 35.76 parts of MTBE, 0.62 parts of isobutylene and 43.43 parts of linear butenes was fed to distillation column C-1; from the top of C-1 (line 6) there were obtained 44.95 parts of a fraction having the following percent composition:

| | |
|---|---|
| isobutylene (% by weight) | = 1.4 |
| methanol (% by weight) | = 2.0 |
| linear olefines (% by weight) | = 96.6; | from the bottom of C-1 (line 5) 35.76 parts of MTBE and 7.56 parts of methanol were discharged, which parts, joined with 37.00 parts of isobutylene and 43.43 parts of linear butenes (2), were fed to reactor R-2 wherein they reacted over Amberlyst 15 at the temperature of 60° C and with LHSV of 40.

In R-2 the isobutylene-methanol molar ratio was 2.8.

The effluent stream (7) from reactor R-2 was constituted by 55.60 parts of MTBE, 0.35 parts of methanol, 23.38 parts of isobutylene, 53.43 parts of linear butenes and 0.99 parts of diisobutylene. The reaction product (7) was fed to distillation column C-2 from the top of which through (3) 23.38 parts of isobutylene, 43.43 parts of linear butenes and 0.35 parts of methanol were discharged, said compounds being recycled to reactor R-I, and from the bottom of which, through (8), 56.59 parts of MTBE of 98.25% purity were withdrawn.

The total conversion of methanol was 96% with a selectivity of 100% while isobutylene conversion was 98% with a selectivity of 97%.

EXAMPLE 2

This example is different from the foregoing one because of the use of the scheme illustrated in FIG. 2.

32.12 parts by weight of methanol (1) were joined with the effluent stream (3) from the top of column C-2 constituted by 0.98 parts of methanol, 40.73 parts of linear butenes and 23.94 parts of isobutylene and with a portion (4) of the feed olefines (2), said portion being constituted by 16.44 parts of isobutylene and 16.77 parts of linear butenes.

The reaction mixture in which the isobutylene-methanol ratio was 0.72 was fed to reactor R-1 with LHSV of 5 wherein it reacted over Amberlyst 15 at 60° C and at a pressure sufficient to maintain the system in the liquid state.

The reaction product (6) constituted by 10.67 parts of methanol, 1.11 parts of isobutylene, 57.50 parts of linear butenes and 61.70 parts of MTBE was fed to distillation column C-1 from the top of which we obtained (line 10) 59.67 parts of a fraction having the following percent composition:

| | |
|---|---|
| isobutylene (% by weight) | = 1.9 |
| methanol (% by weight) | = 1.8 |
| linear butenes (% by weight) | = 96.3 | and from the bottom of which we obtained (line 7) 9.61 parts of methanol and 61.70 parts of MTBE.

The bottom product of C-1 (7) joined with 39.66 parts of isobutylene and 40.73 parts of linear butenes (line 5) constituting the remaining portion of the olefinic feed (2) was reacted in R-2 at 60° C and LHSV of 40. In this case the isobutylene/methanol ratio was 2.35. The reaction product (8) constituted by 0.98 parts of methanol, 85.45 parts of MTBE, 23.94 parts of isobutylene, 40.73 parts of linear butenes and 0.88 parts of diisobutylene was sent to distillation column C-2 distilling as top product (line 3) 0.98 parts of methanol, 23.94 parts of isobutylene and 40.73 parts of linear butenes which were recycled to R-1.

From the bottom of C-2 (line 9) we recovered 86.33 parts of MTBE at 99% purity.

The total conversion of methanol was 96.7% with a selectivity of 100%; the isobutylene conversion was 98% with a selectivity of 98%.

EXAMPLE 3

The feed to reactor R-2 of the foregoing example was reacted at two different temperatures and at three different space velocities obtaining the following results:

| Temperature | | 60° C | | | 70° C | |
|---|---|---|---|---|---|---|
| LHSV | 3 | 8.5 | 40 | 3 | 8.5 | 40 |
| Total conversion of isobutylene | 61 | 55 | 44 | 63 | 55 | 45.5 |
| Conversion of isobutylene to MTBE | 41.5 | 46.5 | 41 | 43 | 42.5 | 37 |
| Selectivity | 68 | 83 | 93 | 68 | 77.5 | 82 |

LHSV = space velocity expressed as volumes of liquid feed per volume of catalyst per hour.

What we claim is:

1. In a process for the production of methyl tert-butyl ether by reacting isobutylene with methanol at a pressure sufficient to maintain the liquid phase in the presence of a catalyst consisting of an acid ion exchange resin, the improvement which comprises the steps of:
    (a) reacting in a first reactor in the presence of the catalyst at a temperature of from 60°–70° C (i) methanol and (ii) a mixture comprised of isobutylene, linear olefins, and methanol, the total quantity of methanol being in stoichiometric excess of the quantity of isobutylene;
    (b) subjecting the product of step (a) to distillation to obtain an off gas comprised of linear olefins and less than 2 percent of isobutylene and a bottoms product comprised of methanol and tert-butyl ether;
    (c) reacting in a second reactor in the presence of the catalyst at a temperature of from 60° to 70° C the bottoms product of step (b) with a mixture comprised of isobutylene and linear olefins, the space velocity of the mixture being in the range of 20 to 50 LHSV and the respective total quantities of methanol and isobutylene reacted in steps (a) and (c) being stoichiometrically equivalent; and
    (d) subjecting the product of step (c) to distillation to produce an off gas comprised of isobutylene, linear olefins, and methanol, and a bottoms product comprised of methyl tert-butyl ether, the off gas being recycled as feed to the reactor in step (a).

2. The process of claim 1 wherein the mixture comprised of isobutylene, linear olefins, and methanol in step (a) consists essentially of the off gas from step (d).

3. The process of claim 1 wherein the mixture comprised of isobutylene, linear olefins, and methanol in step (a) consists essentially of the off gas from step (d) and a portion of a mixture comprising isobutylene and linear olefins, the remainder of said mixture being introduced in step (c).

4. The process of claim 1 wherein the ratio by weight of isobutylene to methanol in step (a) is from about 0.62 to 0.72.

5. The process of claim 1 wherein the ratio by weight of isobutylene to methanol in step (c) is from about 2.35 to 2.8.

6. The process of claim 1 wherein the space velocity of the mixture in step (a) is 5 LHSV.

* * * * *